(12) United States Patent
Ohsumi et al.

(10) Patent No.: US 6,908,905 B2
(45) Date of Patent: Jun. 21, 2005

(54) N-SUBSTITUTED PYRAZOLE-O-GLYCOSIDE DERIVATIVES AND THERAPEUTIC AGENT FOR DIABETES CONTAINING THE SAME

(75) Inventors: Koji Ohsumi, Kawasaki (JP); Hiroyuki Matsueda, Kawasaki (JP); Toshihiro Hatanaka, Kawasaki (JP); Nozomu Ishida, Kawasaki (JP); Yoko Kageyama, Kawasaki (JP); Katsumi Maezono, Kawasaki (JP); Nobuo Kondo, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/692,738

(22) Filed: Oct. 27, 2003

(65) Prior Publication Data

US 2004/0110936 A1 Jun. 10, 2004

Related U.S. Application Data

(63) Continuation of application No. PCT/JP02/04238, filed on Apr. 26, 2002.

(30) Foreign Application Priority Data

Apr. 27, 2001 (JP) ........................ 2001-131265
Aug. 31, 2001 (JP) ........................ 2001-263717

(51) Int. Cl.[7] ............... A61K 31/70; A61K 31/7028; A61K 31/7042
(52) U.S. Cl. ............... 514/25; 514/406; 514/407; 514/866; 536/17.4; 548/373.1
(58) Field of Search ............... 514/25, 406, 407, 514/866; 536/17.4; 548/373.1

(56) References Cited

U.S. PATENT DOCUMENTS 6,815,428 B2 * 11/2004 Ohsumi et al. ............ 514/25

FOREIGN PATENT DOCUMENTS

| JP | 2003-12686 | 1/2003 |
| WO | WO 01/16147 | 3/2001 |
| WO | WO 02/36602 | 5/2002 |
| WO | WO 02/053573 | 7/2002 |
| WO | WO 02/068439 | 9/2002 |
| WO | WO 02/068440 | 9/2002 |
| WO | WO 02/098893 | 12/2002 |
| WO | WO 03/020737 | 3/2003 |

* cited by examiner

*Primary Examiner*—James O. Wilson
*Assistant Examiner*—Jason H. Johnsen
(74) *Attorney, Agent, or Firm*—Oblon, Spivak, McClelland, Maier & Neustadt, P.C.

(57) ABSTRACT

The present invention relates to pyrazole derivatives represented by the following formulas and analogues thereof, which can be used for a therapeutic agent for diabetes.

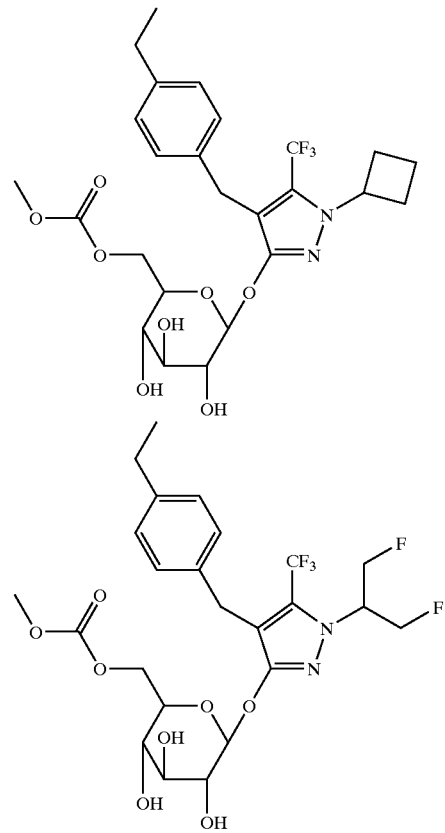

20 Claims, No Drawings

N-SUBSTITUTED PYRAZOLE-O-GLYCOSIDE DERIVATIVES AND THERAPEUTIC AGENT FOR DIABETES CONTAINING THE SAME

CROSS-REFERENCE TO RELATED APPLICATIONS

The present application is a Continuation application of PCT/JP02/04238 filed on Apr. 26, 2002.

BACKGROUND OF THE INVENTION

The present invention relates to novel pyrazole derivatives and a therapeutic agent for diabetes containing such compounds as the active ingredient.

$Na^+$-dependent glucose transporter (SGLT) is a membrane protein which transports glucose, and SGLT-1 and SGLT-2 are known. In the renal uriniferous tubules, the SGLT-2 is mainly expressed. Glucose that is filtered in glomeruli is reabsorbed at the renal uriferous tubules via SGLT, and the glucose taken is reused in the body through the bloodstream. When the SGLT-2 is inhibited, the amount of glucose reabsorbed at renal uriniferous tubles lowers, and the glucose is excreted in urine. As a result, it is considered that the level of blood glucose decreases. Therefore, it is considered that an SGLT inhibitor which is effective when administered orally is useful for treating diabetes.

There is known 3-(benzo[b]furan-5-yl)-2',6'-dihydroxy-4'-methylpropiophenone 2'-O-(6-O-methoxycarbonyl-β-D-glucopyranoside) as a compound that can inhibit the SGLT and promote the action of urinary sugar excretion in the animals (J. Med. Chem., 42, 5311–5324, 1999). Oral administration of the above-mentioned compound to the rat indicates the increase in the amount of sugar excreted in urine and the decrease in the level of blood sugar (Diabetes, Vol. 48, pp. 1794–1800, 1999). However, there is the shortcoming that the dose needed to exhibit the efficacy is as large as 100 mg/kg. Further, the evaluation system by a glucose tolerance test shows that compounds disclosed in WO 0116147 are effective at a dose of 10 mg/kg in the rats by intravenous administration or subcutaneous administration. However, there is no description about the efficacy of those compounds by oral administration.

DISCLOSURE OF THE INVENTION

It is an object of the present invention to provide novel pyrazole derivatives.

It is another object of the present invention to provide a pharmaceutical composition comprising the above-mentioned novel compounds.

It is still another object of the present invention to provide a therapeutic agent for diabetes comprising the above-mentioned novel compounds.

It is a further object of the present invention to find a therapeutic agent for diabetes which can easily be synthesized and has less toxicity and excellent therapeutic effect, and to provide the therapeutic agent for diabetes as a pharmaceutical product.

It is a still further object of the present invention to provide an agent for inducing urinary sugar excretion which comprises the above-mentioned novel compounds.

Also, it is a still further object of the present invention to provide the use of the above-mentioned novel compounds for reducing renal glucose reabsorption at renal uriniferous tubules.

The inventors of the present invention have synthesized various derivatives (1A) and (1B) wherein glucose (namely, β-D-glucopyranose) is bonded to a pyrazole nucleus, and intensively explored the effect of those derivatives on urinary excretion of sugar. As a result, it has been found that an outstanding effect on urinary excretion of sugar is exhibited in tests on animals particularly by the compounds of general formula (1A) or (1B) wherein Z represents a cyclic alkyl group which may have a substituent(s), a cyclic unsaturated alkyl group which may have a substituent(s), a lower alkyl group having an unsaturated bond, a lower alkyl group having a cyclic alkyl group which may have a substituent(s), or a lower alkyl group having a cyclic unsaturated alkyl group which may have a substituent(s). The present invention has been thus accomplished. The inventors of the present invention have also found that oral administration of a compound represented by general formula (I) wherein Z' is a halo lower alkyl group indicates an outstanding effect on urinary excretion of sugar in tests on animal, and thus accomplished the present invention. These compounds have not synthesized, and therefore, such compounds are entirely novel pyrazole-O-glycoside derivatives.

Namely, the present invention provides pyrazole derivatives represented by the following general formula (1A) or (1B), or pharmaceutically acceptable salts thereof:

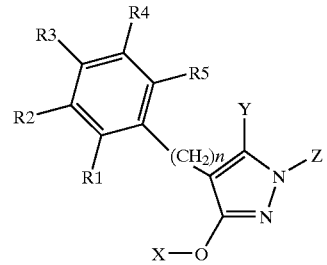

(1A)

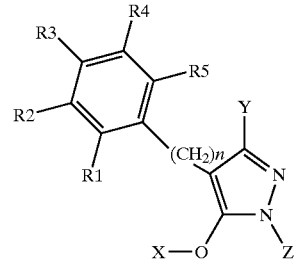

(1B)

wherein X represents β-D-glucopyranosyl group (wherein one or more hydroxyl groups may be acylated); Y represents a lower alkyl group or a perfluoro lower alkyl group; Z represents a cyclic alkyl group which may have a substituent (s), a cyclic unsaturated alkyl group which may have a substituent(s), a lower alkyl group having a cyclic alkyl group which may have a substituent(s), or a lower alkyl group having a cyclic unsaturated alkyl group which may have a substituent(s); R1 to R5 may be the same or different and each represent a hydrogen atom, a lower alkyl group, a perfluoro lower alkyl group, a lower alkoxyl group, a perfluoro lower alkoxyl group, a lower alkylthio group, a perfluoro lower alkylthio group, a lower alkylamino group, a halogeno group, a lower alkanoyl group, an alkenyl group, a cyclic alkenyl group, an alkynyl group, a phenyl group which may have a substituent(s), or a lower alkoxycarbonyl group; and n is an integer of 0 to 3.

The present invention also provides pyrazole-O-glycoside derivatives represented by the following general formula (I) and pharmaceutically acceptable salts thereof:

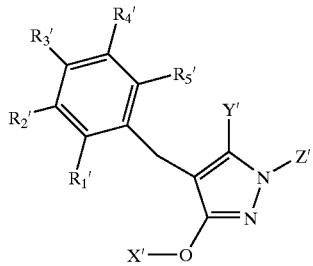

(I)

wherein X' represents β-D-glucopyranosyl group (wherein one or more hydroxyl groups may be acylated); Y' represents a hydrogen atom, a lower alkyl group, a fluoro lower alkyl group or a perfluoro lower alkyl group; Z' represents a halo lower alkyl group; and $R_1'$ to $R_5'$ may be the same or different and each represent a hydrogen atom, a halogeno group, a lower alkyl group, a halo lower alkyl group, a perfluoro lower alkyl group, a lower alkoxyl group, a perfluoro lower alkoxyl group, a lower alkylthio group, a perfluoro lower alkylthio group, a lower alkylamino group, a lower alkanoyl group, a lower alkenyl group, or a lower alkynyl group.

The present invention provides a pharmaceutical composition comprising as the active ingredient the above-mentioned pyrazole derivatives or pharmaceutically acceptable salts thereof.

The present invention also provides a therapeutic agent for diabetes comprising as the active ingredient the above-mentioned pyrazole derivatives or pharmaceutically acceptable salts.

The present invention also provides an agent for inducing urinary excretion of sugar comprising as the active ingredient the above-mentioned pyrazole derivatives or pharmaceutically acceptable salts thereof.

Further, the present invention provides the use of the above-mentioned pyrazole derivatives or pharmaceutically acceptable salts thereof for reducing renal glucose reabsorption at renal uriniferous tubules.

BEST MODE FOR CARRYING OUT THE INVENTION

The term "lower alkyl group" in the present specification means an alkyl group having 1 to 6 carbon atoms, preferably 1 to 3 carbon atoms.

The term "lower alkenyl group" in the present specification means an alkenyl group having 2 to 6 carbon atoms, preferably 2 to 4 carbon atoms.

The term "lower alkynyl group" in the present specification means an alkynyl group having 2 to 6 carbon atoms, preferably 2 to 4 carbon atoms.

The terms "alkyl", "alkenyl" and "alkynyl" used in the alkyl group, perfluoro lower alkyl group, lower alkoxyl group, perfluoro lower alkoxyl group, lower alkylthio group, perfluoro lower alkylthio group, lower alkylamino group, lower alkanoyl group, lower alkenyl group, or lower alkynyl group may be straight-chain or branched.

Examples of the alkyl group include methyl group, ethyl group, propyl group, butyl group, pentyl group, hexyl group, isopropyl group, isobutyl group, isopentyl group, isohexyl group.

The halo lower alkyl group includes a fluoro lower alkyl group, a chloro lower alkyl group, and a bromo lower alkyl group. There can be employed, for example, fluoromethyl group, fluoroethyl group, fluoropropyl group, fluorobutyl group, fluoropentyl group, fluorohexyl group, chloromethyl group, chloroethyl group, chloropropyl group, chlorobutyl group, chloropentyl group, chlorohexyl group, bromomethyl group, bromoethyl group, bromopropyl group, bromobutyl group, bromopentyl group, bromohexyl group.

Specific examples of the fluoro lower alkyl group include monofluoromethyl group, difluoromethyl group, 2-fluoroethyl group, 2,2-difluoroethyl group, 2,2,2-trifluoroethyl group, 3,3,3-trifluoropropyl group, 1,3-difluoroisopropyl group, 1,1,1-trifluoro-2-propyl group, 1,1,1,3,3,3-hexafluoroisopropyl group.

Examples of the perfluoro lower alkyl group include trifluoromethyl group, pentafluoroethyl group, heptafluoropropyl group.

Examples of the lower alkoxyl group—include methoxy group, ethoxy group, propyloxy group, isopropyloxy group, butyloxy group.

Examples of the perfluoro lower alkoxyl group include trifluoromethoxy group, pentafluoroethoxy group, heptafluoropropyloxy group.

Examples of the lower alkylthio group include methylthio group, ethylthio group, propylthio group.

Examples of the perfluoro lower alkylthio group include trifluoromethylthio group, pentafluoroethylthio group, heptafluoropropylthio group.

Examples of the lower alkylamino group include methylamino group, ethylamino group, propylamino group, dimethylamino group, diethylamino group, diisopropylamino group.

Examples of the lower alkanoyl group are acetyl group, propionyl group.

Examples of the lower alkenyl group include vinyl group, propenyl group, 2-methyl-1-propenyl group.

Examples of the lower alkynyl group include ethynyl group, 2-methylethynyl group.

Examples of the aralkyl group include benzyl group, benzyl group which may have a substituent(s), phenethyl group, phenethyl group which may have a substituent(s). Examples of the substituent herein used are a lower alkyl group, a lower alkoxyl group, a halogeno group, an amino group, a lower alkylamino group.

Examples of the halogeno group are fluorine atom, chlorine atom, bromine atom, and iodine atom.

Examples of the lower alkoxycarbonyl group include methoxycarbonyl group, ethoxycarbonyl group, and isopropoxycarbonyl group.

The "cyclic alkyl group which may have a substituent(s)" means a cyclic alkyl group having 3 to 7 carbon atoms which may have a substituent(s). For example, cyclopropyl group, cyclobutyl group, cyclopentyl group, cyclohexyl group, cycloheptyl group can be used. The ring in the above groups may have a substituent(s) such as methyl group, ethyl group, methoxy group, ethoxy group, fluorine atom, chlorine atom, bromine atom. The number of the substituent and the position of the substitution are not particularly limited.

The "cyclic unsaturated alkyl group which may have a substituent(s)" includes cyclopentenyl group and cyclohexenyl group. The ring in the above groups may have a substituent(s) such as methyl group, ethyl group, methoxy group, ethoxy group, fluorine atom, chlorine atom, bromine atom. The number of the substituent and the position of the substitution are not particularly limited. The number, kind, and position of the unsaturated bond are not particularly limited, either.

The "lower alkyl group having a cyclic alkyl group which may have a substituent(s)" includes, for example, cyclobutylmethyl group, cyclobutylethyl group, cyclopentylmethyl group, cyclopentylethyl group, cyclohexylmethyl group, cyclohexylethyl group. The ring in the above groups may have a substituent(s) such as methyl group, ethyl group, methoxy group, ethoxy group, fluorine atom, chlorine atom, bromine atom. The number of the substituent and the position of the substitution are not particularly limited.

The "lower alkyl group having a cyclic unsaturated alkyl group which may have a substituent(s)" includes cyclopentenylmethyl group and cyclohexenylmethyl group. The ring in the above groups may have a substituent(s) such as methyl group, ethyl group, methoxy group, ethoxy group, fluorine atom, chlorine atom, bromine atom. The number of the substituent and the position of the substitution are not particularly limited. The number, kind, and position of the unsaturated bond are not particularly limited, either.

The groups used for acylating the hydroxyl group include acyl group and carbamate group. Examples of the acyl group are acetyl group, propionyl group, benzoyl group, pivaloyl group. Examples of the carbamate group are methyl carbonate group, ethyl carbonate group, propyl carbonate group, isopropyl carbonate group, phenyl carbonate group.

In the above-mentioned general formula (1A) or (1B), one or more hydroxyl groups in the β-D-glucopyranosyl group which is a group represented by X may be acylated, in particular, with a group selected from an alkanoyl group having 2 to 20 carbon atoms, a lower alkoxycarbonyl group and a benzoyl group. Examples of such groups are 6-acetyl-β-D-glucopyranosyl group and 6-carbomethoxy-β-D-glucopyranosyl group.

As the group represented by X, β-D-glucopyranosyl group, 6-acetyl-β-D-glucopyranosyl group and 6-carbomethoxy-β-D-glucopyranosyl group are preferable. Further, β-D-glucopyranosyl group is particularly preferable.

As the group represented by Y, the perfluoro lower alkyl group having 1 to 6 carbon atoms, in particular, trifluoromethyl group is preferable.

As the group represented by Y, the lower alkyl group having 1 to 6 carbon atoms, in particular, methyl group is particularly preferable.

A preferable group represented by Z is a cyclic alkyl group which may have a substituent(s). In particular, a cyclic alkyl group having 3 to 7 carbon atoms is more preferable, and cyclobutyl group and cyclopentyl group are especially preferable. As the group represented by Z, the lower alkyl group having an unsaturated bond is also preferable, and an alkyl group having 2 to 6 carbon atoms containing an unsaturated bond therein is more preferable. In particular, allyl group and vinyl group are preferable. As the group represented by Z, the cyclic unsaturated alkyl group which may have a substituent(s) is preferable, a cyclic alkyl group having 4 to 7 carbon atoms is more preferable, and in particular, cyclopentenyl group and cyclohexenyl group are most preferable.

Preferably, the group represented by R1 to R5 may be a lower alkyl group having 1 to 6 carbon atoms, and a lower alkylthio group having 1 to 6 carbon atoms, in particular, methyl group, ethyl group, methylthio group and ethylthio group.

It is particularly preferable that n represent an integer of 1.

In general formula (1A) or (1B), —it is preferable that Y is trifluoromethyl group.

Further, in general formula (1A) or (1B), it is preferable that Y is trifluoromethyl group and n is an integer of 1.

Furthermore, in general formula (1A) or (1B), it is preferable that Y is trifluoromethyl group, n is an integer of 1, and X is β-D-glucopyranosyl group (wherein one or more hydroxyl groups may be acylated with a group selected from the group consisting of an alkanoyl group having 2 to 20 carbon atoms, a lower alkoxycarbonyl group and a benzoyl group).

Also, it is preferable in general formula (1A) or (1B) that Y is trifluoromethyl group, n is an integer of 1, and X—is β-D-glucopyranosyl group.

Further, in general formula (1A), it is preferable that Y is trifluoromethyl group, n—is an integer of 1, and X—is 6-acetyl-β-D-glucopyranosyl group.

In general formula (1A) or (1B), it is preferable that Y is trifluoromethyl group, n is an integer of 1, and X is 6-carbomethoxy-β-D-glucopyranosyl group.

With respect to the general formula (1A) or (1B), the compounds or pharmaceutically acceptable salts thereof described below are also preferable:

1'-cyclobutyl-4'-[(4-ethylphenyl)methyl]-5'-trifluoromethyl-1H-pyrazole-3'-O-β-D-glucopyranoside,
1'-cyclopentyl-4'-[(4-ethylphenyl)methyl]-5'-trifluoromethyl-1H-pyrazole-3'-O-β-D-glucopyranoside,
1'-cyclohexyl-4'-[(4-ethylphenyl)methyl]-5'-trifluoromethyl-1H-pyrazole-3'-O-β-D-glucopyranoside,
1'-(3-cyclopenten-1-yl)-4'-[(4-ethylphenyl)methyl]-5'-methyl-1H-pyrazole-3'-O-β-D-glucopyranoside,
1'-cyclobutyl-4'-[(4-ethylphenyl)methyl]-5'-methyl-1H-pyrazole-3'-O-β-D-glucopyranoside,
1'-cyclopentyl-4'-[(4-ethylphenyl)methyl]-5'-methyl-1H-pyrazole-3'-O-β-D-glucopyranoside,
1'-cyclohexyl-4'-[(4-ethylphenyl)methyl]-5'-methyl-1H-pyrazole-3'-O-β-D-glucopyranoside,
1'-(3-cyclopenten-1-yl)-4'-[(4-ethylphenyl)methyl]-5'-methyl-1H-pyrazole-3'-O-β-D-glucopyranoside,
1'-cyclobutyl-4'-[(4-ethylphenyl)methyl]-5'-trifluoromethyl-1H-pyrazole-3'-O-(6-carbomethoxy)-β-D-glucopyranoside,
1'-cyclopentyl-4'-[(4-ethylphenyl)methyl]-5'-trifluoromethyl-1H-pyrazole-3'-O-(6-carbomethoxy)-β-D-glucopyranoside, 1'-cyclohexyl-4'-[(4-ethylphenyl)methyl]-5'-trifluoromethyl-1H-pyrazole-3'-O-(6-carbomethoxy)-β-D-glucopyranoside, 1'-(3-cyclopenten-1-yl)-4'-[(4-ethylphenyl)methyl]-5'-methyl-1H-pyrazole-3'-O-(6-carbomethoxy)-β-D-glucopyranoside, 1'-cyclobutyl-4'-[(4-ethylphenyl)methyl]-5'-methyl-1H-pyrazole-3'-O-(6-carbomethoxy)-β-D-glucopyranoside, 1'-cyclopentyl-4'-[(4-ethylphenyl)methyl]-5'-methyl-1H-pyrazole-3'-O-(6-carbomethoxy)-β-D-glucopyranoside, 1'-cyclohexyl-4'-[(4-ethylphenyl)methyl]-5'-methyl-1H-pyrazole-3'-O-(6-carbomethoxy)-β-D-glucopyranoside, and 1'-(3-cyclopenten-1-yl)-4'-[(4-ethylphenyl)methyl]-5'-methyl-1H-pyrazole-3'-O-(6-carbomethoxy)-β-D-glucopyranoside.

Of the above-mentioned examples, the following compounds or pharmaceutically acceptable salts thereof are particularly preferable:

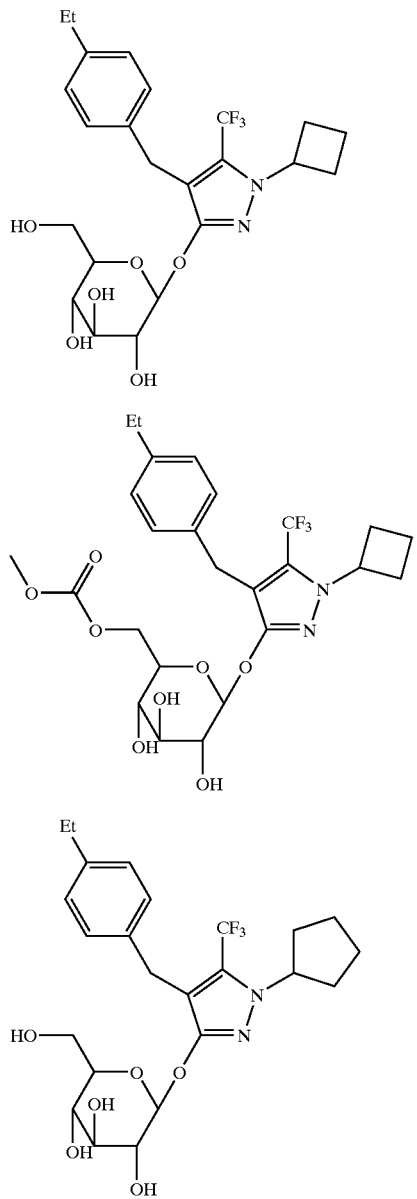

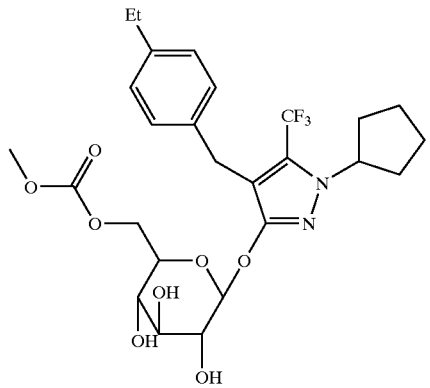

In the above-mentioned general formula (I), one or more hydroxyl groups in the β-D-glucopyranosyl group which is a group represented by X' may be acylated or carbamated. In particular, one or more hydroxyl groups in the above-mentioned group may be acylated with a group selected from the group consisting of an alkanoyl group having 2 to 20 carbon atoms, preferably 2 to 6 carbon atoms, a lower alkoxycarbonyl group, and a benzoyl group. Examples of such groups are 6-acetyl-β-D-glucopyranosyl group and 6-carbomethoxy-β-D-glucopyranosyl group.

As the group represented by X', in particular, β-D-glucopyranosyl group, 6-acetyl-β-D-glucopyranosyl group, 6-carbomethoxy-β-D-glucopyranosyl group, and 6-carboethoxy-β-D-glucopyranosyl group are preferable.

As the group represented by Y', the lower alkyl group and the perfluoro lower alkyl group, especially trifluoromethyl group and methyl group are preferable.

As the group represented by Z', a halo lower alkyl group having 2 to 6 carbon atoms is preferable. In particular, the alkyl group in the above-mentioned halo lower alkyl group may be preferably branched. With respect to the substitution by a halogeno group, mono-substitution or poly-substitution is suitable. The position of a substitution with a halogeno group, is not particularly limited. In particular, it is preferable to use a fluoro lower alkyl group; more preferable to use monofluoroethyl, monofluoropropyl, monofluoroisopropyl, difluoroisopropyl, and trifluoroisopropyl; and most preferable to use 1,3-difluoroisopropyl group. In addition, the group represented by Z' may be any other groups than the perfluoro lower alkyl group.

The group represented by $R_1'$ to $R_5'$ may be a lower alkyl group having 1 to 6 carbon atoms, a lower alkylthio group having 1 to 6 carbon atoms, a lower alkoxyl group having 1 to 6 carbon atoms, or a halogeno group. In particular, methyl group, ethyl group, methoxy group, ethoxy group, and fluorine atom are preferable. In particular, it is most preferable that $R_3'$ is any of the above-mentioned groups.

In the general formula (I), it is preferable that X' is β-D-glucopyranosyl group (wherein one or more hydroxyl groups may be acylated with a group selected from the group consisting of an alkanoyl group having 2 to 20 carbon atoms, a lower alkoxycarbonyl group and a benzoyl group), Y' is trifluoromethyl group, and Z' is a halo lower alkyl group.

It is also preferable in general formula (I) that X' is β-D-glucopyranosyl group (wherein one or more hydroxyl groups may be acylated with a group selected from the group consisting of an alkanoyl group having 2 to 20 carbon atoms, a lower alkoxycarbonyl group and a benzoyl group), Y' is trifluoromethyl group, and Z' is a fluoro lower alkyl group.

In general formula (I), it is preferable that X' is β-D-glucopyranosyl group (wherein one or more hydroxyl groups may be acylated with a group selected from the group consisting of an alkanoyl group having 2 to 20 carbon atoms, a lower alkoxycarbonyl group and a benzoyl group), Y' is methyl group, and Z' is a halo lower alkyl group.

Also, it is preferable in general formula (1) that X' is β-D-glucopyranosyl group (wherein one or more hydroxyl groups may be acylated with a group selected from the group consisting of an alkanoyl group having 2 to 20 carbon atoms, a lower alkoxycarbonyl group and a benzoyl group), Y' is methyl group, and Z' is a fluoro lower alkyl group.

Further, it is preferable in general formula (I) that X' is 6-acetyl-β-D-glucopyranosyl group, Y' is trifluoromethyl group, and Z' is a fluoro lower alkyl group.

It is also preferable in general formula (I) that X' is 6-carbomethoxy-β-D-glucopyranosyl group, Y' is trifluoromethyl group, and Z' is a fluoro lower alkyl group.

Further, it is preferable in general formula (I) that X' is 6-acetyl-β-D-glucopyranosyl group, Y' is methyl group, and Z' is a fluoro lower alkyl group.

Furthermore, it is also preferable in general formula (I) that X' is 6-carbomethoxy-β-D-glucopyranosyl group, Y' is methyl group, and Z' is a fluoro lower alkyl group.

With respect to the general formula (I), the compounds or pharmaceutically acceptable salts thereof described below are also preferable:

4-((4-ethylphenyl)methyl)-1-(1,3-difluoro-2-propyl)-5-(trifluoromethyl)-1H-pyrazole-3-O-β-D-glucopyranoside, 4'-((4'-ethylphenyl)methyl)-1'-(1',3'-difluoro-2'-propyl)-5'-(trifluoromethyl)-1H-pyrazole-3'-O-(6-O-acetyl-β-D-glucopyranoside), 4'-((4'-ethylphenyl)methyl)-1'-(1',3'-difluoro-2'-propyl)-5'-(trifluoromethyl)-1H-pyrazole-3'-O-(6-O-methoxycarbonyl-β-D-glucopyranoside), 4-((4-ethylphenyl)methyl)-1-(1,3-difluoro-2-propyl)-5-methyl-1H-pyrazole-3-O-β-D-glucopyranoside, 4'-((4'-ethylphenyl)methyl)-1'-(1',3'-difluoro-2'-propyl)-5'-methyl-1H-pyrazole-3'-O-(6-O-acetyl-β-D-glucopyranoside), 4'-((4'-ethylphenyl)methyl)-1'-(1',3'-difluoro-2'-propyl)-5'-methyl-1H-pyrazole-3'-O-(6-O-methoxycarbonyl-β-D-glucopyranoside), 4-((4-ethylphenyl)methyl)-1-(2-monofluoroethyl)-5-(trifluoromethyl)-1H-pyrazole-3-O-β-D-glucopyranoside, 4'-((4'-ethylphenyl)methyl)-1'-(2'-monofluoroethyl)-5'-(trifluoromethyl)-1H-pyrazole-3'-O-(6-O-acetyl-β-D-glucopyranoside), 4'-((4'-ethylphenyl)methyl)-1'-(2'-monofluoroethyl)-5'-(trifluoromethyl)-1H-pyrazole-3'-O-(6-O-methoxycarbonyl-β-D-glucopyranoside), 4-((4-ethylphenyl)methyl)-1-(2-monofluoroethyl)-5-methyl-1H-pyrazole-3-O-β-D-glucopyranoside, 4'-((4'-ethylphenyl)methyl)-1'-(2'-monofluoroethyl)-5'-methyl-1H-pyrazole-3'-O-(6-O-acetyl-β-D-glucopyranoside), 4'-((4'-ethylphenyl)methyl)-1'-(2'-monofluoroethyl)-5'-methyl-1H-pyrazole-3'-O-(6-O-methoxycarbonyl-β-D-glucopyranoside), 4-((4-ethylphenyl)methyl)-1-(3-monofluoropropyl)-5-(trifluoromethyl)-1H-pyrazole-3-O-β-D-glucopyranoside, 4'-((4'-ethylphenyl)methyl)-1'-(3'-monofluoropropyl)-5'-(trifluoromethyl)-1H-pyrazole-3'-O-(6-O-acetyl-β-D-glucopyranoside), 4'-((4'-ethylphenyl)methyl)-1'-(3'-monofluoropropyl)-5'-(trifluoromethyl)-1H-pyrazole-3'-O-(6-O-methoxycarbonyl-β-D-glucopyranoside), 4-((4-ethylphenyl)methyl)-1-(3-monofluoropropyl)-5-methyl-1H-pyrazole-3-O-β-D-glucopyranoside, 4'-((4'-ethylphenyl)methyl)-1'-(3'-monofluoropropyl)-5'-methyl-1H-pyrazole-3'-O-(6-O-acetyl-β-D-glucopyranoside), 4'-((4'-ethylphenyl)methyl)-1'-(3'-monofluoropropyl)-5'-methyl-1H-pyrazole-3'-O-(6-O-methoxycarbonyl-β-D-glucopyranoside), (II)

(III)

With respect to the method for preparing the pyrazole derivative (1A) or (1B) according to the present invention, for example, wherein X represents β-D-glucopyranosyl group, the derivative can be prepared by the method shown below.

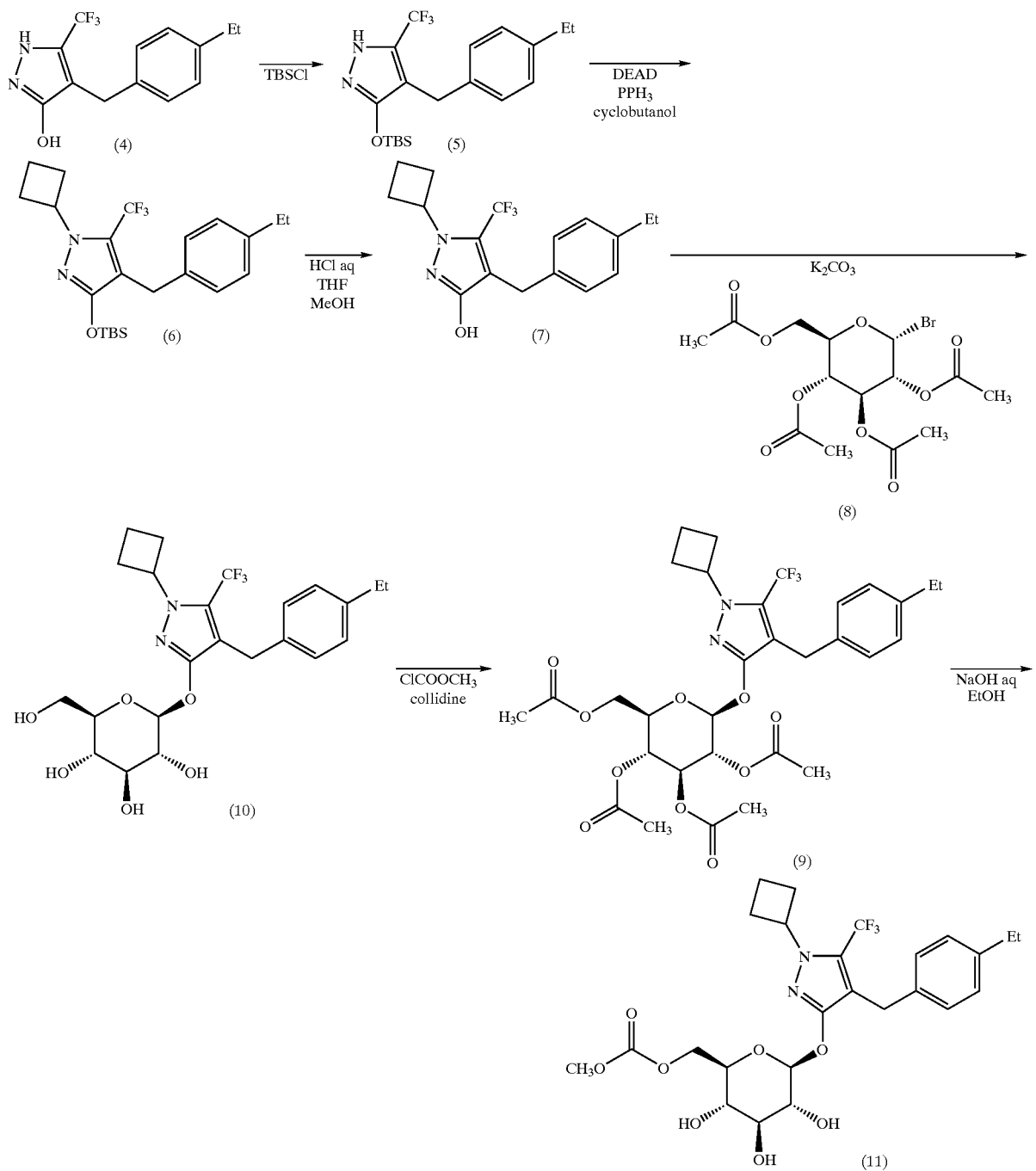

A compound (11) of the present invention can be obtained by the following method. For example, a hydroxyl group of 1,2-dihydro-4-[(4-ethylphenyl)methyl]-5-(trifluoromethyl)-3H-pyrazol-3-one (4) is protected using tert-butyl dimethylsilyl chloride to obtain a compound (5). A nitrogen atom on the pyrazole is allowed to react with cyclobutyl alcohol in accordance with the Mitsunobu reaction, thereby producing a compound (6). After the deprotection of the TBS group in the compound (6) with diluted hydrochloric acid, the obtained compound is allowed to react with 2,3,4,6-tetra-O-acetyl-α-D-glucopyranosyl bromide (8) overnight in the presence of potassium carbonate in a mixture of chloroform and water, and the resultant reaction product is subjected to a purification procedure by using, for example, chromatography, so that a tetra-O-acetyl intermediate (9) is obtained. Subsequently, the intermediate is deprotected in an aqueous solution of sodium hydroxide, whereby a compound (10) is obtained. The primary hydroxyl group of the obtained compound (10) is allowed to react with methyl chlorocarbonate, thereby obtaining the intended compound (11).

With respect to the methods for preparing the pyrazole derivatives (I) according to the present invention wherein X' represents β-D-glucopyranosyl group, for example, the derivative can be prepared by the method shown below.

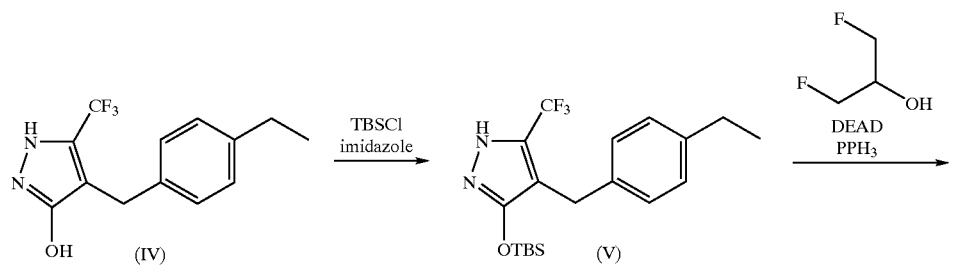
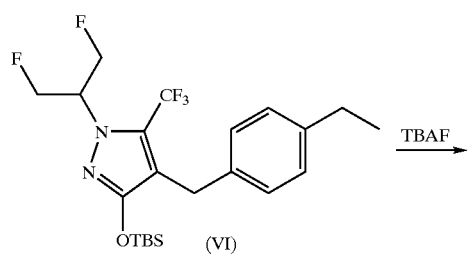
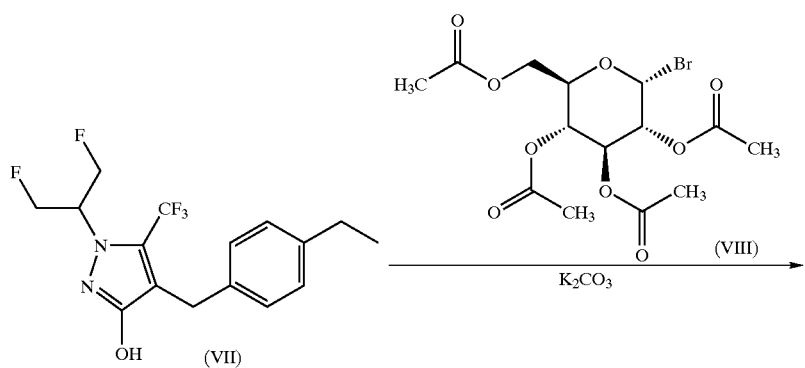
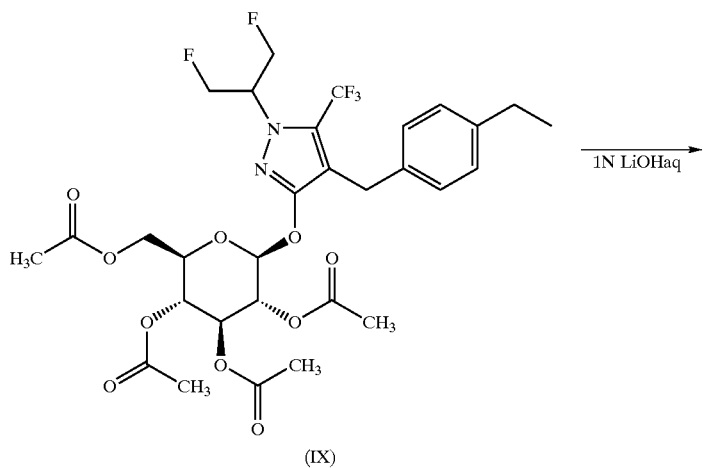

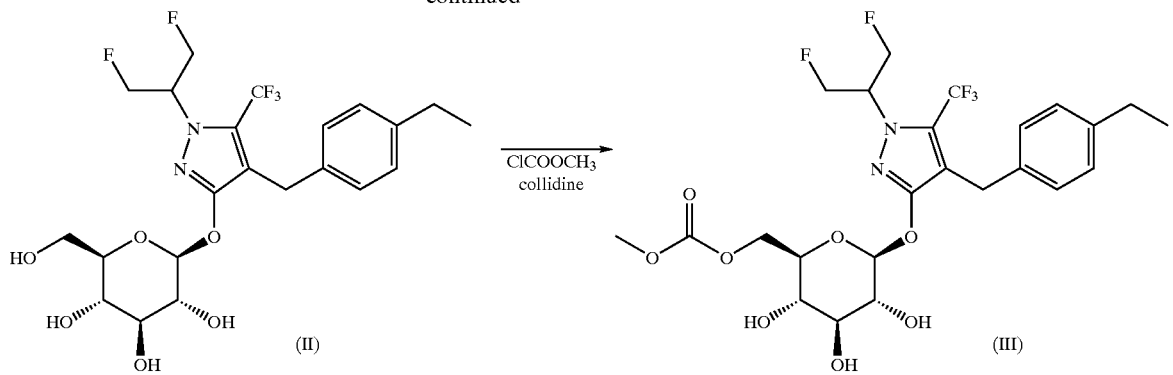

The compound represented by general formula (I) according to the present invention can be obtained using as the starting material, for example, 1,2-dihydro-4-[(4-ethylphenyl)methyl]-5-(trifluoromethyl)-3H-pyrazol-3-one (IV) (prepared by the method described in J. Med. Chem 1996, 39, 3920–3928). More specifically, a hydroxyl group of a compound (IV) is protected using TBS group to obtain a compound (V). Thereafter, a nitrogen atom on the pyrazole is subjected to selective alkylation by the Mitsunobu reaction, thereby obtaining a compound (VI). Subsequently, the TBS group of the compound (VI) is deprotected to obtain a compound (VII). The compound (VII) is allowed to react with acetobromoglucose (VIII) in the presence of potassium carbonate at room temperature, thereby obtaining a glycoside (IX). Thereafter, deprotection of the acetyl protecting group of the glycoside (IX) with a 1N lithium hydroxide aqueous solution can produce pyrazole glucoside (II). The pyrazole glucoside (II) is dissolved in collidine and allowed to react with methyl chlorocarbonate at −10° C., thereby obtaining a compound (III) wherein a hydroxyl group at the 6th position of the glucose is replaced by methyl carbonate.

The pyrazole-O-glucoside derivatives according to the present invention which may be prepared by the above-mentioned method can easily be separated from the reaction mixture and purified by using the conventional isolation and purification means such as extraction from a solvent, chromatography, and crystallization.

Further, the hydroxyl group of the compound of the present invention may be substituted with an appropriate substituent which can be replaced by hydroxyl group in vivo. For example, acyl group and carbamate group can be used as the substituent for the hydroxyl group. The acyl group includes, for example, an alkanoyl group having 2 to 20 carbon atoms and a benzoyl group; and the carbamate group includes, for example, a lower alkoxycarbonyl group.

In the case where the compound represented by general formula (1A), (1B) or (I) according to the present invention can be formed into salts thereof, any salts that are pharmaceutically acceptable can be used. For example, when an acidic group exists in the formula, the combination with the acidic group can give the following salts: ammonium salts; salts of alkali metals such as sodium and potassium; salts of alkaline earth metals such as calcium and magnesium; aluminum salts and zinc salts; salts of organic amines such as triethylamine, ethanolamine, morpholine, piperidine and dicyclohexylamine; and salts of basic amino acids such as arginine and lysine. When a basic group exists in the formula, the combination with the basic group can give the following salts: salts of inorganic acids such as hydrochloric acid, sulfuric acid and phosphoric acid; salts of organic carboxylic acids such as oxalic acid, acetic acid, citric acid, malic acid, benzoic acid, maleic acid, fumaric acid, tartaric acid, succinic acid and glutamic acid; and salts of organic sulfonic acids such as methanesulfonic acid and p-toluenesulfonic acid. Such salts can be formed by mixing the compound of general formula (1A), (1B) or (I) with an acid or base as required in appropriate proportions in a solvent and a dispersant. Alternatively, the salts can also be obtained by cation or anion exchange from other salts in different forms.

The present invention includes the compound represented by general formula (1A), (1B) or (I) in the form of solvates, for example, hydrates, alcohol adducts.

According to the present invention, an inhibitor comprising as the active ingredient the compound represented by general formula (1A), (1B) or (I), or the salt thereof can be used for a pharmaceutical composition, in particular, for treatment of diabetes.

In the present invention, when the above-mentioned pyrazole-O-glycoside derivative is applied to the pharmaceutical composition, for example, to a therapeutic agent for diabetes, the agent can be administered orally or parenterally (i.e., intramuscularly, subcutaneously or intravenously, and in the form of suppositories). As for the compound of formula (I), oral administration is preferred. The daily dose in adults taken for the above-mentioned purpose, which is determined depending on the intended therapeutic effect, administration method, treatment period, and age and weight of the individual, is usually in the range of 1 µg to 10 g by oral administration, and in the range of 0.01 µg to 1 g by parenteral administration. When the compound of formula (I) is given by oral administration, the daily dose is preferably in the range of 0.5 mg to 1 g, more preferably in the range of 1.0 mg to 500 mg.

Further, when the pyrazole-O-glycoside derivative of the present invention is prepared into a formulation for oral administration, the formulation is shaped into, for example, a tablet, powder, pill, granule, capsule, suppository, solution, sugar-coated tablet, depot preparation, syrup by the conventional methods after the addition of an excipient and other agents such as a binder, disintegrant, lubricant, coloring agent, taste- and odor-masking agent to the derivative of the present invention. Examples of the excipient include lactose, corn starch, sucrose, glucose, sorbitol and crystalline cellulose. Examples of the binder include polyvinyl alcohol, polyvinyl ether, ethyl cellulose, methyl cellulose, gum arabic, tragacanth, gelatin, shellac, hydroxypropyl cellulose, hydroxypropyl starch, polyvinylpyrrolidone. Examples of the disintegrant include starch, agar, gelatin powder, crystalline cellulose, calcium carbonate, sodium hydrogen carbonate, calcium citrate, dextran, pectin. Examples of the lubricant include magnesium stearate, talc, polyethylene glycol, silica, hydrogenated vegetable oil. With respect to the coloring agent, any materials that are permitted to be added to pharmaceutical compositions can be used. Examples of the taste- and odor-masking agent include cocoa powder, menthol, aromatic acid, mentha oil, borneol, cinnamon bark powder. Such tablets and granules may appropriately be coated with sugar, gelatin and other coating agents, if necessary.

For the preparation of an injection, a solution for subcutaneous, intramuscular, or intravenous injection is prepared according to the conventional methods by the addition of a pH adjuster, a buffering agent, a stabilizing agent, a preserving agent, if necessary.

EXAMPLES

The following Examples will further illustrate the present invention. They are preferred embodiments of the present invention, which by no means limit the invention.

Example 1

Synthesis of 1'-cyclobutyl-4'-[(4-ethylphenyl)methyl]-5'-trifluoromethyl-1H-pyrazole-3'-O-β-D-glucopyranoside Step 1

Synthesis of 4-[(4-ethylphenyl)methyl]-5-trifluoromethyl-3-O-t-butyl dimethylsilyl-1H-pyrazole 4.76 g (17.6 mmol) of 1,2-dihydro-4-[(4-ethylphenyl)methyl]-5-trifluoromethyl-3H-pyrazol-3-one (prepared by the method described in J. Med. Chem 1996, 39, 3920–3928) and 1.57 g (23.1 mmol) of imidazole were dissolved in 20 ml of dimethylformamide. To this mixture was added 2.98 g (19.8 mmol) of t-butyl dimethylsilyl chloride, and the resultant mixture was stirred at room temperature for 30 minutes. After adding 100 ml of water to the above-mentioned mixture, the reaction mixture was extracted with a mixed solvent of ethyl acetate and hexane (2:1) three times. The resultant organic layer was washed with water, dried over sodium sulfate and concentrated, so that 6.9 g (17.9 mmol, quantitative yield) of the intended product was obtained.

$^1$H-NMR (300 MHz, CDCl$_3$) δ: 0.21 (6H, s), 0.93 (9H, s), 1.19 (3H, t, J=7.6 Hz), 2.59 (2H, q, J=7.6 Hz), 3.74 (2H, s), 7.09 (4H, m).

ESI-MS (m/z): 269 [(M−TBS)$^-$]

Step 2

Synthesis of 1-cyclobutyl-4-[(4-ethylphenyl)methyl]-5-trifluoromethyl-3-O-t-butyl dimethylsilyl-1H-pyrazole 2.5 g (6.5 mmol) of 4-[(4-ethylphenyl)methyl]-5-trifluoromethyl-3-O-t-butyl dimethylsilyl-1H-pyrazole, 1.9 g (7.2 mmol) of triphenylphosphine, and 0.71 g (9.8 mmol) of cyclobutanol were dissolved in 15 ml of anhydrous tetrahydrofuran, and the obtained mixture was stirred at room temperature. To the thus obtained solution, 3.4 ml (7.5 mmol) of a 40% toluene solution of diethyl azodicarboxylate was added slowly. After 20 minutes, the above-mentioned reaction mixture was concentrated and 20 ml of hexane was added thereto. After the resultant precipitate was separated by filtration, the filtrate was concentrated and subjected to a silica gel column for purification, using hexane alone and a mixed solvent of ethyl acetate and hexane at a ratio of 5:95 successively. Thus, 1.4 g (3.3 mmol) of the intended product was obtained (51%).

$^1$H-NMR (300 MHz, CDCl$_3$) δ: 0.27 (6H, s), 0.96 (9H, s), 1.20 (3H, t, J=7.5 Hz), 2.26–2.34 (2H, m), 2.59 (2H, q, J=7.5 Hz), 2.54–2.67 (2H, m), 3.72 (2H, s), 4.67 (1H, quint, J=8.1 Hz), 7.06 (2H, d, J=8.5 Hz), 7.10 (2H, d, J=8.5 Hz).

ESI-MS (m/z): [323 (M−TBS)$^-$]

Step 3

Synthesis of 1-cyclobutyl-4-[(4-ethylphenyl)methyl]-5-trifluoromethyl-1H-pyrazole 1.4 g (3.3 mmol) of 1-cyclobutyl-4-[(4-ethylphenyl)methyl]-5-trifluoromethyl-3-O-t-butyl dimethylsilyl-1H-pyrazole was dissolved in a mixture of 25 ml of tetrahydrofuran and 5 ml of methanol. To the above solution was added 5 ml of a 1M HCl aqueous solution, and the mixture thus prepared was stirred overnight at room temperature. To the resultant mixture was added 100 ml of water. The reaction mixture was extracted with 10 ml of ethyl acetate three times, dried over anhydrous sodium sulfate and concentrated, and thereafter, purified with a silica gel column using hexane alone and a mixed solvent of ethyl acetate and hexane at a ratio of 5:95 successively to give 0.84 g (2.6 mmol) of the intended product (78%).

$^1$H-NMR (300 MHz, CDCl$_3$) δ: 1.20 (3H, t, J=7.5 Hz), 1.70–1.90 (2H, m), 2.28–2.36 (2H, m), 2.59 (2H, q, J=7.5 Hz), 2.55–2.68 (2H, m), 3.80 (2H, s), 4.75 (1H, pseudo quint, J=8.1 Hz), 7.10 (2H, d, J=8.8 Hz), 7.18 (2H, d, J=8.8 Hz).

ESI-MS (m/z): [325 (M+H)$^+$], [323 (M−H)$^-$]

Step 4

Synthesis of 1'-cyclobutyl-4'-[(4-ethylphenyl)methyl]-5'-trifluoromethyl-1H-pyrazole-3'-O-(2,3,4,6-tetraacetyl)-β-D-glucopyranoside 2 ml of water and 10 ml of chloroform were added to a mixture of 0.84 g (2.6 mmol) of 1-cyclobutyl-4-[(4-ethylphenyl)methyl]-5-trifluoromethyl-1H-pyrazole, 1.5 g (3.7 mmol) of 2,3,4,6-O-tetraacetyl-α-D-glucopyranosyl bromide, 0.10 g (0.32 mmol) of benzyl tri-n-butyl ammonium chloride, and 3.23 g (23 mmol) of potassium carbonate. The thus obtained mixture was stirred at room temperature for 18 hours. The resultant organic layer was purified with a silica gel column using hexane alone and a mixed solvent of hexane and ethyl acetate at a ratio of 10:1 to 2:1 successively to give 2.1 g of the intended compound in the form of a crude product, which product was subjected to the following reaction.

$^1$H-NMR (300 MHz, CDCl$_3$) δ: 1.19 (3H, t, J=7.6 Hz), 1.72–1.84 (2H, m), 1.89 (3H, s), 2.03 (3H, s), 2.04 (3H, s), 2.06 (3H, s), 2.29–2.38 (2H, m), 2.58 (2H, q, J=7.6 Hz), 2.58–2.68 (2H, m), 3.72 (2H, s), 3.88 (1H, ddd, J=9.9, 4.9, 2.3 Hz), 4.11–4.17 (1H, m), 4.26 (1H, dd, J=12.3, 9.4 Hz), 4.70–4.76 (1H, m), 5.15–5.22 (1H, m), 5.28–5.32 (2H, m), 5.64–5.66 (1H, m), 7.06 (4H, s).

ESI-MS (m/z): [655 (M+H)+]

Step 5

Synthesis of 1'-cyclobutyl-4'-[(4-ethylphenyl)methyl]-5'-trifluoromethyl-1H-pyrazole-3'-O-β-D-glucopyranoside After 2.1 g of the crude product of 1'-cyclobutyl-4'-[(4-ethylphenyl)methyl]-5'-trifluoromethyl-1H-pyrazole-3'-O-(2,3,4,6-tetraacetyl)-β-D-glucopyranoside was dissolved in 20 ml of ethanol, the obtained mixture was stirred at room temperature with 4 ml of a 4N sodium hydroxide aqueous solution being added thereto. One hour later, 50 ml of a saturated sodium chloride aqueous solution and 10 ml of water were added to the above-mentioned mixture. The resultant mixture was extracted with 20 ml of ethyl acetate three times, concentrated, and purified with a silica gel column using dichloromethane alone and a mixed solvent of methanol and dichloromethane at a ratio of 10:90 successively. Thus, 0.63 g (1.3 mmol) of the intended product was obtained (50%).

$^1$H-NMR (300 MHz, CD$_3$OD) δ: 1.18 (3H, t, J=7.6 Hz), 1.79–1.89 (2H, m), 2.28–2.36 (2H, m), 2.57 (2H, q, J=7.6 Hz), 2.60–2.72 (2H, m), 3.37–3.45 (4H, m), 3.65–3.71 (1H, m), 3.81 (2H, s), 3.81–3.86 (1H, m), 5.39–5.41 (1H, m), 7.06 (4H, s).

MS(ESI) (m/z): [487 (M+H)+], [485 (M−H)−]

Example 2

Synthesis of 1'-cyclobutyl-4'-[(4-ethylphenyl)methyl]-5'-trifluoromethyl-1H-pyrazole-3'-O-(6-carbomethoxy)-β-D-glucopyranoside 0.18 g (0.32 mmol) of 1'-cyclobutyl-4'-[(4-ethylphenyl)methyl]-5'-trifluoromethyl-1H-pyrazole-3'-O-β-D-glucopyranoside was dissolved in 2.0 ml of 2,4,6-collidine and cooled to −50° C. With the addition of 0.035 ml (0.45 mmol) of methyl chlorocarbonate, the temperature of the obtained mixture was returned to room temperature over a period of 0.5 hours. After 27 hours, 20 ml of ethyl acetate and 20 ml of a 1M hydrochloric acid aqueous solution were added to the above-mentioned reaction mixture, and the reaction mixture was extracted with ethyl acetate. The reaction product was dried and concentrated, and thereafter purified with a silica gel column using a mixed solvent of hexane and ethyl acetate at a ratio of 1:1 to 1:3 and ethyl acetate alone successively. Thus, 0.12 g (0.20 mmol) of the intended product was obtained (62%).

$^1$H-NMR (300 MHz, CDCl$_3$) δ: 1.20 (3H, t, J=7.6 Hz), 1.71–1.86 (2H, m), 2.29–2.38 (2H, m), 2.48 (1H, d, J=2.6 Hz), 2.60–2.68 (2H, m), 2.60 (2H, q, J=7.6 Hz), 2.68 (1H, s), 2.72 (1H, s), 3.49–3.65 (4H, m), 3.72 (1H, d, J=15.2 Hz), 3.79 (3H, s), 3.87 (1H, d, J=15.2 Hz), 4.32 (1H, dd, J=12.0, 2.1 Hz), 4.48 (1H, dd, J=12.0, 4.1 Hz), 4.74 (1H, pseudo quint, J=8.4 Hz), 5.22 (1H, d, J=7.9 Hz), 7.10 (4H, s).

MS(ESI) (m/z): [545 (M+H)+], [543 (M−H)−]

Example 3

Synthesis Step 1 of 1'-cyclopentyl-4'-[(4-ethylphenyl)methyl]-5'-trifluoromethyl-1H-pyrazole-3'-O-β-D-glucopyranoside

Synthesis of 1-cyclopentyl-4-[(4-ethylphenyl)methyl]-5-trifluoromethyl-3-O-t-butyl dimethylsilyl-1H-pyrazole The step 2 in Example 1 was repeated except that cyclobutanol was replaced by cyclopentanol, so that the intended product was obtained (86%).

$^1$H-NMR (300 MHz, CDCl$_3$) δ: 0.23 (6H, s), 0.94 (9H, s), 1.20 (3H, t, J=7.6 Hz), 1.55–1.70 (2H, m), 1.80–2.05 (6H, m), 2.59 (2H, q, J=7.6 Hz), 3.72 (2H, s), 4.54–4.66 (1H, m), 7.06 (2H, d, J=8.4 Hz), 7.11 (2H, d, J=8.4 Hz).

Step 2

Synthesis of 1-cyclopentyl-4-[(4-ethylphenyl)methyl]-5-trifluoromethyl-1H-pyrazole The intended product was obtained from 1-cyclopentyl-4-[(4-ethylphenyl)methyl]-5-trifluoromethyl-3-O-t-butyl dimethylsilyl-1H-pyrazole in the same manner as in the step 3 of Example 1 (95%).

$^1$H-NMR (300 MHz, CDCl$_3$) δ: 1.20 (3H, t, J=7.6 Hz), 1.50–1.70 (2H, m), 1.80–2.10 (6H, m), 2.60 (2H, q, J=7.6 Hz), 3.79 (2H, s), 4.53–4.68 (1H, m), 7.09 (2H, d, J=8.1 Hz), 7.17 (2H, d, J=8.1 Hz), 10.1–10.2 (1H, br).

MS(ESI) (m/z): 339 [(M+H)+], 337 [(M−H)−]

Step 3

Synthesis of 1'-cyclopentyl-4'-[(4-ethylphenyl)methyl]-5'-trifluoromethyl-1H-pyrazole-3'-O-(2,3,4,6-tetraacetyl)-β-D-glucopyranoside The intended product was obtained as a crude product from 1-cyclopentyl-4-[(4-ethylphenyl)methyl]-5-trifluoromethyl-1H-pyrazole in the same manner as in the step 4 of Example 1.

$^1$H-NMR (300 MHz, CDCl$_3$) δ: 1.19 (3H, t, J=7.6 Hz), 1.60–1.68 (2H, m), 1.88 (3H, s), 2.02 (3H, s), 2.04 (3H, s), 2.06 (3H, s), 1.98–2.0 (2H, m), 2.58 (2H, q, J=7.6 Hz), 3.72 (2H, s), 3.80–3.85 (1H, m), 4.11 (1H, dd, J=8.5, 3.8 Hz), 4.25 (1H, dd, J=12.5, 4.8 Hz), 4.65 (1H, pseudo quint, J=7.0 Hz), 5.14–5.20 (1H, m), 5.24–5.30 (2H, m), 5.56–5.59 (1H, m), 7.06 (4H, s).

MS(ESI) m/z [669 (M+H)+]

Step 4

Synthesis of 1-cyclopentyl-4'-[(4-ethylphenyl)methyl]-5'-trifluoromethyl-1H-pyrazole-3'-O-β-D-glucopyranoside The intended product was obtained by the hydrolysis of the crude product of 1'-cyclopentyl-4'-[(4-ethylphenyl)methyl]-5'-trifluoromethyl-1H-pyrazole-3'-O-(2,3,4,6-tetraacetyl)-β-D-glucopyranoside in the same manner as in the step 5 of Example 1 (90%).

$^1$H-NMR (300 MHz, CD$_3$OD) δ: 1.19 (3H, t, J=7.6 Hz), 1.62–1.68 (2H, m), 1.87–2.04 (6H, m), 2.57 (2H, q, J=7.6 Hz), 3.32–3.45 (3H, m), 3.67 (1H, dd, J=12.0, 5.0 Hz), 3.78–3.82 (3H, m), 4.70 (1H, pseudo quint, J=6.9 Hz), 5.30–5.37 (1H, m), 7.06 (4H, s).

MS(ESI) m/z [501 (M+H)+], [499 (M−H)−]

Example 4

Synthesis of 1'-cyclopentyl-4'-[(4-ethylphenyl)methyl]-5'-trifluoromethyl-1H-pyrazole-3-O-(6-carbomethoxy)-β-D-glucopyranoside The intended product was obtained by allowing 1'-cyclopentyl-4'-[(4-ethylphenyl)methyl]-5'-trifluoromethyl-1H-pyrazole-3-O-β-D-glucopyranoside to react with methyl chlorocarbonate in the same manner as in the step 6 of Example 1 (67%).

$^1$H-NMR (300 MHz, CDCl$_3$) δ: 1.20 (3H, t, J=7.5 Hz), 1.60–1.70 (2H, m), 1.84–1.94 (2H, m), 1.98–2.04 (4H, m), 2.55 (1H, d, J=2.3 Hz), 2.60 (2H, q, J=7.5 Hz), 2.75 (1H, d, J=2.1 Hz), 2.85 (1H, d, J=2.6 Hz), 3.47–3.63 (4H, m), 3.72 (1H, dd, J=15.8, 1.2 Hz), 3.78 (3H, s), 3.87 (1H, d, J=15.8 Hz), 4.36 (1H, dd, J=12.0, 1.8 Hz), 4.45 (1H, dd, J=12.0, 4.1 Hz), 4.66 (1H, pseudo quint, J=6.9 Hz), 5.14 (1H, d, J=7.9 Hz), 7.10 (4H, s).

MS(ESI) m/z [559 (M+H)$^+$], [557 (M−H)$^−$]

The chemical structures of the compounds obtained in Examples 1 to 4 are shown below.

Compound of Example 1

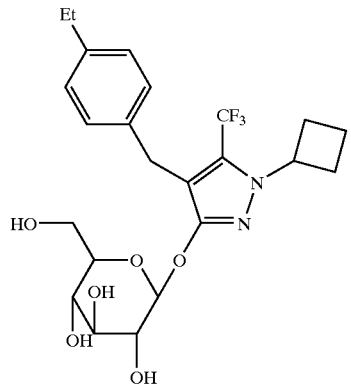

Compound of Example 2

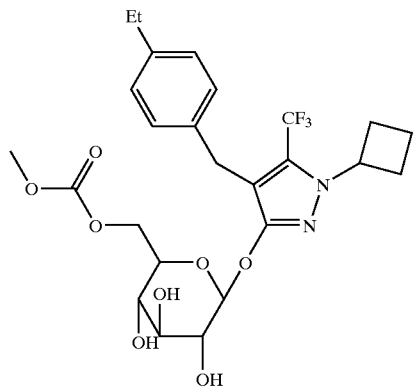

Compound of Example 3

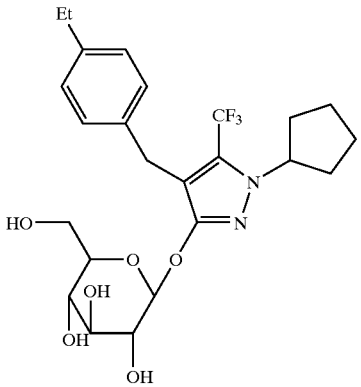

Compound of Example 4

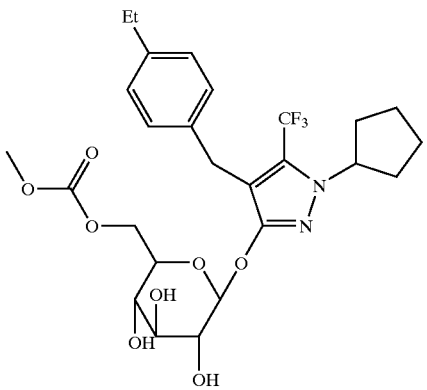

Example 5

Evaluation of Effect on Urinary Excretion of Sugar in Rats

Five-week-old male Wistar rats (purchased from Charles River Japan, Inc.) were housed in metabolic cages for about one week prior to the experiment. A test compound was suspended in olive oil, so that a solution of the compound with a concentration of 20 mg/ml was prepared to have a dose of 5 ml/kg body weight of the rat.

After the rats were not fed for 4 hours, the test compound was orally administered to the rat at a dosage of 100 mg/kg at 11 a.m. Urine of the rat was collected for a given period of time from the time immediately after the administration to 24 hours after the administration, and the urine volume was measured. Subsequently, the glucose concentration in urine was determined by the glucose oxidase method and the daily amount of glucose excreted in urine per individual was calculated.

The results are shown in Table 1.

TABLE 1

| Test Compound | The amount of glucose excreted in urine (mg) |
| --- | --- |
| Compound of Example 2 | 656 |
| Compound of Example 4 | 452 |

Example 6

Step 1

Synthesis of 3-t-butyl dimethylsilyloxy-4-((4-ethylphenyl)methyl)-5-(trifluoromethyl)-1H-pyrazole 15.0 g (55.6 mmol) of 1,2-dihydro-4-((4-ethylphenyl)methyl)-5-(trifluoromethyl)-3H-pyrazol-3-one (4) (prepared by the method described in J. Med. Chem 1996, 39, 3920–3928) was dissolved in 150 ml of dimethylformamide, and cooled to 0° C. Then, 9.3 g (61.1 mmol) of t-butyl dimethylsilyl chloride was added to the above solution in small portions, and thereafter 4.2 g (61.1 mmol) of imidazole was added in small portions. The temperature of the resultant mixture was returned to room temperature and the mixture was stirred for 3 hours. After the addition of water to the reaction mixture, the reaction mixture was extracted with ethyl acetate twice. The resultant organic layer was washed with a saturated sodium chloride aqueous solution, dried over anhydrous sodium sulfate and concentrated, to give 21.4 g (55.6 mmol) of the intended compound (100% yield).

Step 2

Synthesis of 3-t-butyl dimethylsilyloxy-4-((4-ethylphenyl)methyl)-1-(1,3-difluoro-2-propyl)-5-(trifluoromethyl)pyrazole After 2.0 g (5.2 mmol) of 3-t-butyl dimethylsilyloxy-4-((4-ethylphenyl)methyl)-5-(trifluoromethyl)-1H-pyrazole was dissolved in 20 ml of tetrahydrofuran to prepare a solution, 1.6 g (6.25 mmol) of triphenylphosphine and 0.48 ml (6.25 mmol) of 1,3-difluoro-2-propanol were added to the above-mentioned solution. The mixture thus obtained was cooled to 0° C., and 2.84 ml (6.25 mmol) of a 40% toluene solution of diethyl azodicarboxylate was slowly added to the mixture, with the reaction mixture being maintained at a temperature lower than 10° C. The temperature of the reaction mixture was returned to room temperature to carry out the reaction for 2 hours, followed by concentration. To the concentrate thus obtained, a mixed solvent of ethyl acetate and hexane at a ratio of 1:10 was added to precipitate the triphenylphosphine, which was removed from the reaction mixture by filtration. The resultant filtrate was concentrated and purified with a silica gel column using a mixed solvent of ethyl acetate and hexane at a ratio of 1:4. Thus, 1.95 g (4.22 mmol) of the intended difluoroisopropyl compound was obtained. (81% yield)

$^1$H-NMR (300 MHz, DMSO-d6) δ: 0.22 (6H, s), 0.91 (9H, s), 1.13 (3H, t, J=7.5), 2.53 (2H, q, J=7.5), 3.70 (2H, s), 4.65 (2H, brs), 4.81 (3H, brs), 7.02 (2H, d, J=8.4), 7.11 (2H, d, J=8.7).

ESI-MS (m/z): 347 [(M−TBS)$^-$]

Step 3

Synthesis of 1,2-dihydro-4-((4-ethylphenyl)methyl)-1-(1,3-difluoro-2-propyl)-5-(trifluoromethyl)-3H-pyrazol-3-one 1.95 g (4.22 mmol) of 3-t-butyl dimethylsilyloxy-4-((4-ethylphenyl)methyl)-1-(1,3-difluoro-2-propyl)-5-(trifluoromethyl)pyrazole was added to 30 ml of tetrahydrofuran and cooled to 0° C. To the thus obtained mixture, 6.33 ml (6.33 mmol) of a 1M tetrahydrofuran solution of tetrabutylammonium fluoride was slowly added, and the obtained reaction mixture was stirred at room temperature for 30 minutes. The reaction mixture was concentrated and purified with a silica gel column using a mixed solvent of ethyl acetate and hexane at a ratio of 1:4. Thus, 684 mg (1.96 mmol) of the intended product was obtained. (46% yield)

$^1$H-NMR (300 MHz, DMSO-d6) δ: 1.18 (3H, t, J=7.5), 2.58 (2H, q, J=7.5), 3.74 (2H, s), 4.70 (2H, s), 4.86 (3H, brs), 7.08 (2H, d, J=7.8), 7.15 (2H, d, J=8.4), 10.75 (1H, brs).

ESI-MS (m/z): 347 [(M−H)$^-$]

Step 4

Synthesis of 4'-((4'-ethylphenyl)methyl)-1'-(1',3'-difluoro-2'-propyl)-5'-(trifluoromethyl)-1H-pyrazole-3'-O-(2,3,4,6-O-tetraacetyl)-β-D-glucopyranoside 684 mg (1.96 mmol) of 1,2-dihydro-4-((4-ethylphenyl)methyl)-1-(1,3-difluoro-2-propyl)-5-(trifluoromethyl)-3H-pyrazol-3-one was dissolved in 10 ml of chloroform, and to the above solution were added 2.2 g (15.7 mmol) of potassium carbonate and 153 mg (0.49 mmol) of benzyl tributylammonium chloride. Further, 1.2 g (2.94 mmol) of 2,3,4,6-tetraacetyl-α-D-glucopyranosyl bromide was added to the reaction mixture with stirring at room temperature. The obtained reaction mixture was stirred overnight at room temperature. Then, the reaction mixture was neutralized with a 1N hydrochloric acid aqueous solution. After the addition of a saturated sodium chloride aqueous solution, the reaction mixture was extracted with dichloromethane three times. The resultant organic layer was dried, concentrated and purified with a silica gel column using a mixed solvent of ethyl acetate and hexane at a ratio of 1:2. Thus, 2.51 g (3.7 mmol) of the intended product was obtained in the form of a mixture with acetobromoglucose.

$^1$H-NMR (300 MHz, DMSO-d6) δ: 1.13 (3H, t, J=7.5), 1.89 (3H, s), 1.96 (3H, s), 1.97 (3H, s), 2.00 (3H, s), 2.53 (2H, q, J=7.5), 3.69 (2H, s), 3.98–4.04 (1H, m), 4.11–4.19 (3H, m), 4.69 (1H, t, J=5.7), 4.84 (1H, t, J=6.6), 4.96–5.11 (3H, m), 5.46 (1H, t, J=9.6), 5.85 (1H, d, J=8.1), 6.98 (2H, d, J=8.1), 7.09 (2H, d, J=8.1).

ESI-MS (m/z): 679 [(M+H)$^+$]

Step 5

Synthesis of 4-((4-ethylphenyl)methyl)-1-(1,3-difluoro-2-propyl)-5-(trifluoromethyl)-1H-pyrazole-3-O-β-D-glucopyranoside 1.33 g (1.96 mmol) of 4'-((4'-ethylphenyl)methyl)-1'-(1',3'-difluoro-2'-propyl)-5'-(trifluoromethyl)-1H-pyrazole-3'-O-(2,3,4,6-O-tetraacetyl)-β-D-glucopyranoside was dissolved in a mixture of 2 ml of tetrahydrofuran and 2 ml of methanol, and the mixture was stirred at room temperature with the addition thereto of 1N lithium hydroxide. Thirty minutes later, the mixture was neutralized with a 1N hydrochloric acid aqueous solution, and a saturated sodium chloride aqueous solution was added to the mixture. The reaction mixture was extracted with ethyl acetate and dried over anhydrous sodium sulfate. After the resultant product was concentrated, the product was purified with a silica gel column using a mixed solvent of methanol and dichloromethane at a ratio of 1:10. Thus, 1.52 g (2.98 mmol) of the intended product was obtained.

$^1$H-NMR (300 MHz, DMSO-d6) δ: 1.14 (3H, t, J=7.5), 2.54 (2H, q, J=7.5), 3.19–3.25 (4H, m), 3.47 (1H, m), 3.61–3.66 (1H, m), 3.77 (2H, s), 4.47 (1H, t, J=6.0), 4.66 (1H, t, J=4.8), 4.82 (1H, t, J=4.8), 4.83–4.97 (1H, m), 4.97 (1H, d, J=3.0), 5.08 (1H, d, J=4.2), 5.23 (1H, d, J=7.5), 5.36 (1H, d, J=4.8), 7.09 (4H, s).

ESI-MS (m/z): 509 [(M−H)$^-$]

Example 7

Synthesis of 4'-((4'-ethylphenyl)methyl)-1'-(1',3'-difluoro-2'-propyl)-5'-(trifluoromethyl)-1H-pyrazole-3'-O-(6-O-methoxycarbonyl-β-D-glucopyranoside 700 mg (1.37 mmol) of 4-((4-ethylphenyl)methyl)-1-(1,3-difluoro-2-propyl)-5-(trifluoromethyl)-1H-pyrazole-3-O-β-D-glucopyranoside was dissolved in 10 ml of 2,4,6-collidine and cooled to −10° C. To this solution was added 0.13 ml (1.64 mmol) of methyl chlorocarbonate, and the reaction was carried out overnight at −10° C. Then, the reaction mixture was neutralized with a 2N hydrochloric acid solution, and a saturated aqueous solution of sodium chloride was added thereto. The reaction mixture was extracted with ethyl acetate twice. The resultant organic layer was successively washed with a 1N hydrochloric acid solution, a saturated aqueous solution of sodium carbonate and an aqueous solution of sodium chloride, dried and concentrated. The obtained product was then purified with a silica gel column using a mixed solvent of methanol and methylene chloride at a ratio of 5:95. Thus, 526 mg of the intended product was obtained. (68% yield)

$^1$H-NMR (300 MHz, DMSO-d6) δ: 1.14 (3H, t, J=7.5), 2.53 (2H, q, J=7.5), 3.15–3.30 (4H, m), 3.46–3.51 (1H, m), 3.75 (2H, s), 4.12 (1H, d, J=11.7), 4.32 (1H, d, J=11.7), 4.64–4.68 (2H, m), 4.80–4.83 (2H, m), 4.91 (1H, m), 5.21 (1H, d, J=4.2), 5.22 (1H, d, J=7.8), 5.31 (1H, d, J=5.7), 5.46 (1H, d, J=4.8), 7.08 (4H, s).

ESI-MS (m/z): 569 [(M+H)$^+$], 567 [(M−H)$^-$]

The chemical structures of the compounds obtained in Examples 6 and 7 are shown below.

Compound of Example 6

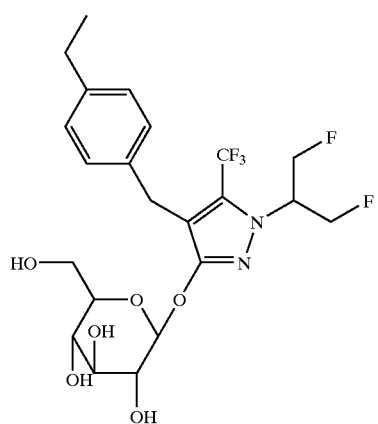

Compound of Example 7

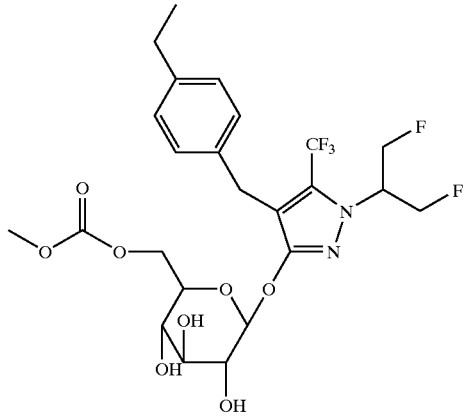

Example 8

Evaluation of Effect on Urinary Excretion of Sugar in Rats

Five-week-old male Wistar rats (purchased from Charles River Japan, Inc.) were housed in metabolic cages for about one week prior to the experiment. A test compound was suspended in olive oil, so that solutions of the compound with concentrations of 6 and 20 mg/ml were prepared to have a dose of 5 ml/kg body weight of the rat. After the rats were not fed for 4 hours, the test compound was orally administered to the rats at a dosage of 10, 30 and 100 mg/kg at 11 a.m. Urine of the rat was collected for a given period of time from the time immediately after the administration to 24 hours after the administration, and the urine volume was measured. Subsequently, the glucose concentration in urine was determined by the glucose oxidase method and the daily amount of glucose excreted in urine per individual was calculated.

As the positive control compound, 3-(benzo[b]furan-5-yl)-2',6'-dihydroxy-4'-methylpropiophenone 2'-O-(6-O-methoxycarbonyl-β-D-glucopyranoside) was used. The results are shown in Table 2.

| Amount of glucose excreted in urine by oral administration in rats (24 hours) | | |
|---|---|---|
| Test Compound | Dosage (mg/kg) | The amount of glucose excreted in urine (mg) |
| Compound of Example 7 | 10 | 136 |
| | 30 | 272 |
| | 100 | 524 |
| Positive Control Compound* | 10 | 2 |
| | 30 | 78 |
| | 100 | 274 |

*Compound Name: 3-(benzo[b]furan-5-yl)-2',6'-dihydroxy-4'-methylpropiophenone 2'-O-(6-O-methoxycarbonyl-β-D-glucopyranoside)

As is apparent from the above, the novel pyrazole derivatives exhibited an excellent effect on urinary sugar excretion. The novel pyrazole derivatives of the present invention, which show excellent antidiabetic properties, is considered to be remarkably useful in the pharmaceutical industry.

What is claimed is:

1. A pyrazole derivative represented by general formula (1A) or (1B), or pharmaceutically acceptable salt thereof:

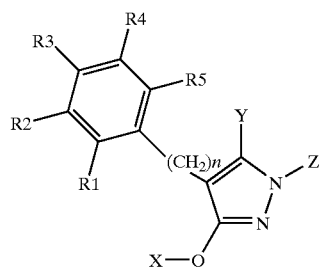
(1A)

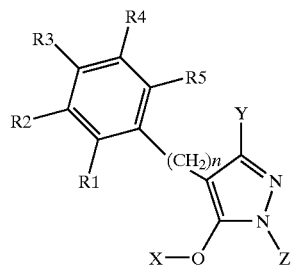
(1B)

wherein X represents β-D-glucopyranosyl group, wherein one or more hydroxyl groups may be acylated; Y represents a lower alkyl group or a perfluoro lower alkyl group; Z represents a cyclic alkyl group which may have a substituent (s), a cyclic unsaturated alkyl group which may have a substituent(s), a lower alkyl group having a cyclic alkyl group which may have a substituent(s), or a lower alkyl group having a cyclic unsaturated alkyl group which may have a substituent(s); R1 to R5 may be the same or different and each represent a hydrogen atom, a lower alkyl group, a perfluoro lower alkyl group, a lower alkoxyl group, a perfluoro lower alkoxyl group, a lower alkylthio group, a perfluoro lower alkylthio group, a lower alkylamino group, a halogeno group, a lower alkanoyl group, an alkenyl group, a cyclic alkenyl group, an alkynyl group, a phenyl group which may have a substituent(s), or a lower alkoxycarbonyl group; and n is an integer of 0 to 3.

2. The pyrazole derivative or pharmaceutically acceptable salt thereof according to claim 1, wherein, in formula (1A) or (1B), Y is trifluoromethyl group.

3. The pyrazole derivative or pharmaceutically acceptable salt thereof according to claim 1, wherein, in formula (1A) or (1B), Y is trifluoromethyl group and n is 1.

4. The pyrazole derivative or pharmaceutically acceptable salt thereof according to claim 1, wherein, in formula (1A) or (1B), Y is trifluoromethyl group, n is 1, and X is β-D-glucopyranosyl group, wherein one or more hydroxyl groups may be acylated with a group selected from the group consisting of an alkanoyl group having 2 to 20 carbon atoms, a lower alkoxycarbonyl group and a benzoyl group.

5. The compound or pharmaceutically acceptable salt thereof according to claim 1, selected from the group consisting of compounds shown below:

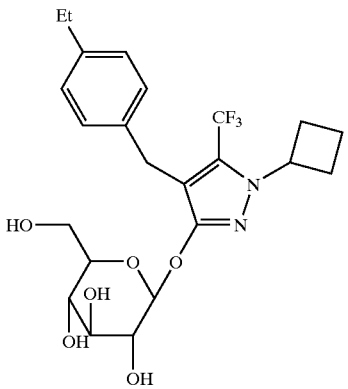
(2)

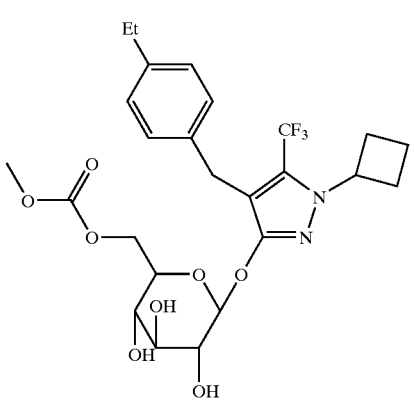
(3)

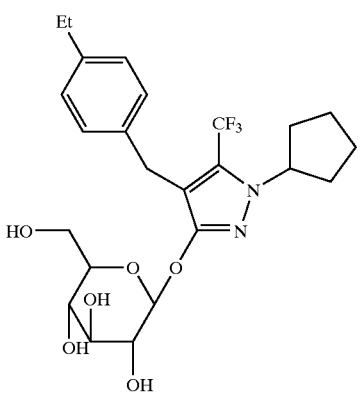
(4)

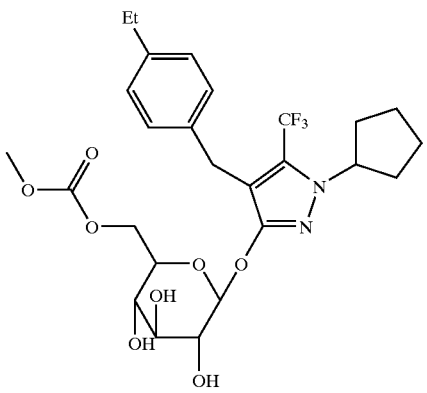
(5)

6. A pharmaceutical composition comprising the pyrazole derivative or pharmaceutically acceptable salt thereof according to claim 1.

7. A therapeutic agent for diabetes comprising the pyrazole derivative or pharmaceutically acceptable salt thereof according to claim 1.

8. An agent for inducing urinary sugar excretion comprising the pyrazole derivative or pharmaceutically acceptable salt thereof according to claim 1.

9. A method for reducing renal glucose reabsorption at renal uriniferous tubules comprising administering the pyrazole derivative or pharmaceutically acceptable salt thereof according to claim 1 to a subject in need thereof.

10. A pyrazole-O-glycoside derivative represented by formula (I) or pharmaceutically acceptable salt thereof:

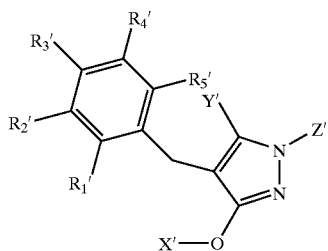

wherein X' represents β-D-glucopyranosyl group, wherein one or more hydroxyl groups may be acylated; Y' represents a hydrogen atom, a lower alkyl group, a fluoro lower alkyl group or a perfluoro lower alkyl group; Z' represents a halo lower alkyl group; and $R_1'$ to $R_5'$ may be the same or different and each represent a hydrogen atom, a halogeno group, a lower alkyl group, a halo lower alkyl group, a perfluoro lower alkyl group, a lower alkoxyl group, a perfluoro lower alkoxyl group, a lower alkylthio group, a perfluoro lower alkylthio group, a lower alkylamino group, a lower alkanoyl group, a lower alkenyl group, or a lower alkynyl group.

11. The pyrazole-O-glycoside derivative or pharmaceutically acceptable salt thereof according to claim 10, wherein, in formula (I), X' is β-D-glucopyranosyl group, wherein one or more hydroxyl groups may be acylated with a group selected from the group consisting of an alkanoyl group having 2 to 20 carbon atoms, a lower alkoxycarbonyl group and a benzoyl group, Y' is trifluoromethyl group, and Z' is a halo lower alkyl group.

12. The pyrazole-O-glycoside derivative or pharmaceutically acceptable salt thereof according to claim 10, wherein, in formula (I), X' is β-D-glucopyranosyl group wherein one or more hydroxyl groups may be acylated with a group selected from the group consisting of an alkanoyl group having 2 to 20 carbon atoms, a lower alkoxycarbonyl group and a benzoyl group, Y' is trifluoromethyl group, and Z' is a fluoro lower alkyl group.

13. The pyrazole-O-glycoside derivative or pharmaceutically acceptable salt thereof according to claim 10, wherein, in formula (I), X' is β-D-glucopyranosyl group, wherein one or more hydroxyl groups may be acylated with a group selected from the group consisting of an alkanoyl group having 2 to 20 carbon atoms, a lower alkoxycarbonyl group and a benzoyl group, Y' is methyl group, and Z' is a halo lower alkyl group.

14. The pyrazole derivative or pharmaceutically acceptable salt thereof according to claim 10, wherein, in formula (I), X' is β-D-glucopyranosyl group, wherein one or more hydroxyl groups may be acylated with a group selected from the group consisting of an alkanoyl group having 2 to 20 carbon atoms, a lower alkoxycarbonyl group and a benzoyl group, Y' is methyl group, and Z' is a fluoro lower alkyl group.

15. The compound or pharmaceutically acceptable salt thereof according to claim 10, selected from the group consisting of compounds shown below:

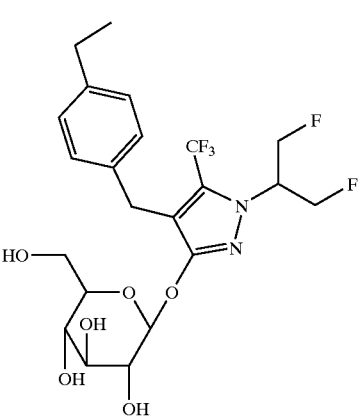

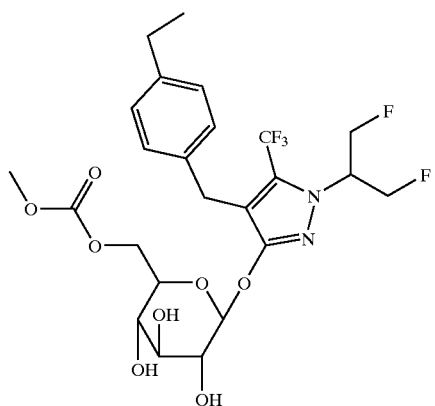

16. A pharmaceutical composition comprising the pyrazole-O-glycoside derivative or pharmaceutically acceptable salt thereof according claim 10.

17. A therapeutic agent for diabetes comprising the pyrazole-O-glycoside derivative or pharmaceutically acceptable salt thereof according to claim 10.

18. A therapeutic agent for diabetes for oral administration, comprising the pyrazole-O-glycoside derivative or pharmaceutically acceptable salt thereof according to claim 10.

19. An agent for inducing urinary sugar excretion comprising the pyrazole-O-glycoside derivative or pharmaceutically acceptable salt thereof according to claim 10.

20. A method for for reducing renal glucose reabsorption at renal uriniferous tubules comprising administering the pyrazole-O-glycoside derivative or pharmaceutically acceptable salt thereof according to claim 10 to a subject in need thereof.

* * * * *